United States Patent [19]
Ohmori et al.

[11] Patent Number: 5,945,544
[45] Date of Patent: Aug. 31, 1999

[54] PROCESS FOR PRODUCTION OF N-VINYLLACTAM

[75] Inventors: Hideki Ohmori; Toshiyuki Fukudome; Tomonori Hakozaki; Tomo Oikawa; Satoshi Kakuta; Hidenobu Oda, all of Ichihara, Japan

[73] Assignee: Maruzen Petrochemical Co., Ltd., Tokyo, Japan

[21] Appl. No.: 09/140,926

[22] Filed: Aug. 27, 1998

[51] Int. Cl.$^6$ ............................................... C07D 207/267
[52] U.S. Cl. .......................... 548/552; 548/555; 546/243; 540/485
[58] Field of Search ..................... 548/552, 555

[56] References Cited

U.S. PATENT DOCUMENTS 4,873,336  10/1989  Liu et al. ................................. 546/243

Primary Examiner—Robert W. Ramsuer
Assistant Examiner—Dominic Keating
Attorney, Agent, or Firm—Melvin I. Stoltz

[57] ABSTRACT

A process for producing an N-vinyllactam by reacting a lactam with acetylene in the presence of a particular catalyst (an alkali metal alcoholate between an alicyclic alcohol and an alkali metal) in a nonaqueous system at an acetylene partial pressure of 0 to 10 kg/cm$^2$·G.

In the above process, the vinylation of lactam with acetylene is conducted at a low acetylene partial pressure in one step while the formation of by-product is kept minimum, whereby a high conversion and a high selectivity of lactam can be achieved.

7 Claims, 1 Drawing Sheet

PROCESS FOR PRODUCTION OF N-VINYLLACTAM

BACKGROUND OF THE INVENTION

(1) Field of the Invention

The present invention relates to a process for producing an N-vinyllactam, wherein a lactam and acetylene can be reacted at a relatively low pressure using a particular catalyst. N-vinyllactams are an important compound used as a material for production of a polyvinyllactam or a copolymer of N-vinyllactam and other vinyl compound.

(2) Description of the Prior Art

N-vinyllactams have been most typically produced by a two-step process. In the first step, an alkali metal hydroxide such as potassium hydroxide is reacted with a lactam to form a corresponding lactam salt catalyst and, in the second step, a lactam is vinylated with acetylene in the presence of said lactam salt catalyst to produce an intended vinyllactam. In this process, however, water is generated in the first step; the water gives rise to lactam ring opening to produce a by-product, namely potassium 4-aminobutyrate, or induces ring-opening polymerization of lactam to produce a by-product polymer; thus, there had been a destruction of catalyst or waste of lactam.

In order to alleviate above problems, various studies were made. For example, in Japanese Patent Application Kokai (Laid-Open) No. 245578/1996, it is described in the Examples (Table 1) that the water formed in the first step and present in the reaction product between lactam and potassium hydroxide, is reduced to 0.1% or less by distillation. However, in this process, relatively high pressures, i.e. an acetylene partial pressure of 18 bar and a total pressure of 20 bar had to be used as seen in the Test Examples of Table 3.

In the reaction of acetylene, as the acetylene partial pressure is higher, the risk of acetylene decomposition and explosion is higher. That is, use of high acetylene partial pressure in reaction is disadvantageous in view of the safety of reaction and the need of special pressure reactor withstanding the pressure. Thus, the process described in the Japanese Patent Application Kokai (Laid-Open) No. 245578/1996 is not fully satisfactory from the standpoint of the industrial applicability.

Meanwhile, in National Publication of International Patent Application No. 501252/1992 is disclosed a process which comprises reacting a lactam and acetylene in the presence of a particular alcoholate catalyst in a nonaqueous system in one step. This process is superior to the process of the Japanese Patent Application Kokai (Laid-Open) No. 245578/1996, because there is no adverse effect by water and the process consists of only one-step.

This process had a problem as well. That is, the conversion of lactam into vinylation product is not sufficiently high even though a reaction is conducted at a relatively high acetylene partial pressure of 100 psig (7 kg/cm$^2$), as described in Examples.

OBJECT AND SUMMARY OF THE INVENTION

The object of the present invention is to achieve, in a reaction of a lactam and acetylene, a high lactam conversion and a high selectivity into N-vinylation product in a one-step simple process, at an as-low-as-possible acetylene partial pressure while formation of by-product is kept minimum.

As a result of an intensive study, the present inventors found out that the above high lactam conversion (the lactam conversion is hereinafter referred to simply as conversion, in some cases) and high selectivity into N-vinylation product (the selectivity into N-vinyllactam is hereinafter referred to simply as selectivity, in some cases) can be achieved in a simple one-step process at a relatively low acetylene partial pressure, by using, in the reaction of a lactam and acetylene, a catalyst of particular structure, i.e. an alkali metal alcoholate between an alicyclic alcohol and an alkali metal.

The present invention lies in:

a process for producing an N-vinyllactam by reacting a lactam with acetylene, which comprises reacting a lactam represented by the following general formula (I):

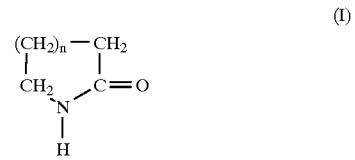

(wherein n is an integer of 1 to 3) with acetylene, in the presence of an alkali metal alcoholate catalyst represented by the following general formula (II):

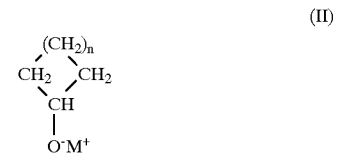

(wherein M is an alkali metal atom, and n is an integer of 2 to 5) at an acetylene partial pressure of 0 to 10 kg/cm$^2$·G (gauge pressure); and a process for producing an N-vinyllactam by reacting a lactam with acetylene, which comprises reacting, in a reactor, a lactam represented by the following general formula (I):

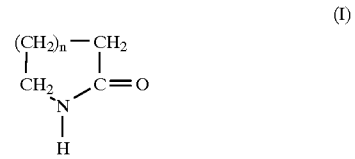

(wherein n is an integer of 1 to 3) with acetylene, in the presence of an alkali metal alcoholate catalyst represented by the following general formula (II):

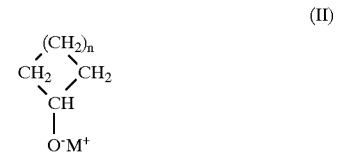

(wherein M is an alkali metal atom, and n is an integer of 2 to 5) at an acetylene partial pressure of 0 to 10 kg/cm$^2$·G (gauge pressure), then continuously taking out the reaction mixture containing the catalyst from the reactor, feeding it into a distillation tower, recovering a fraction composed mainly of an N-vinyllactam from the tower top, taking out a liquid composed mainly of the lactam and the catalyst from the tower bottom, and circulating the liquid into the reactor.

DETAILED DESCRIPTION OF THE INVENTION

Figure 1:
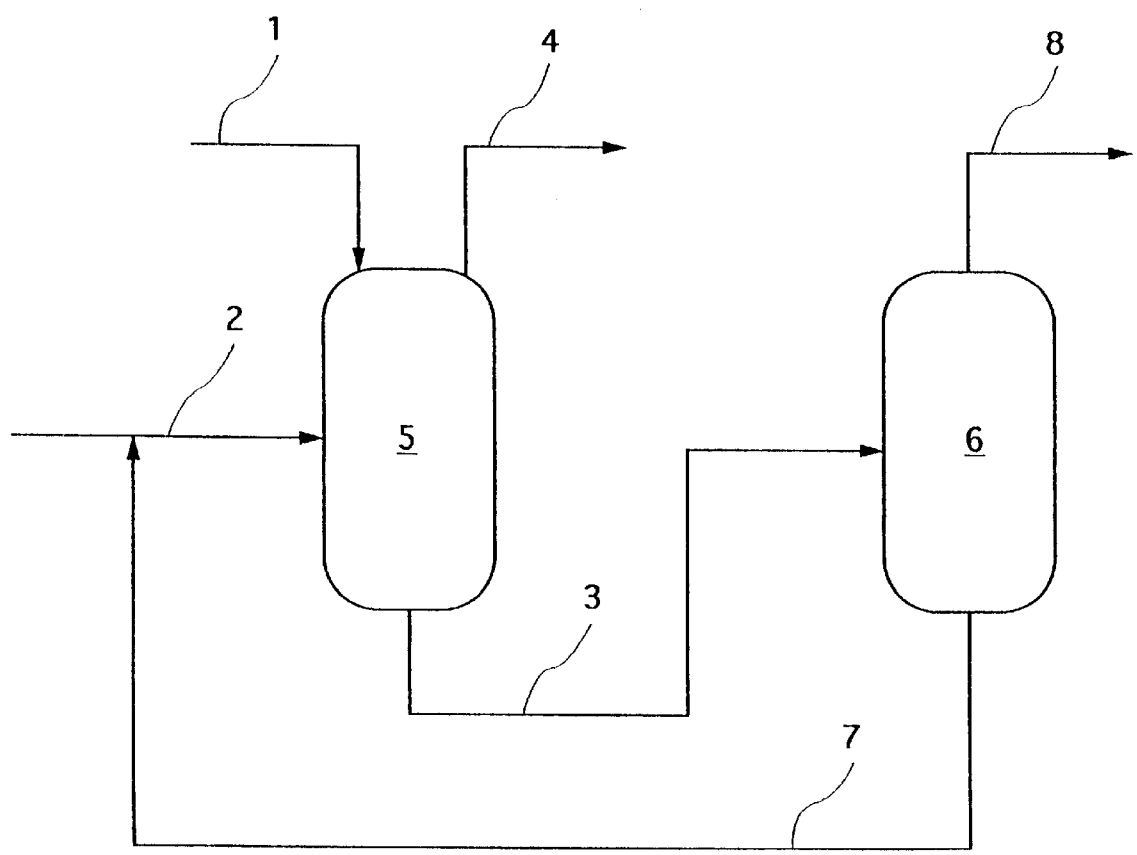
FIG. 1 is a flow chart showing an example of the step used in the present process for continuous production of an N-vinyllactam.

The present is hereinafter described in detail.

The lactam used as a raw material in the present invention is a compound represented by the following general formula (I):

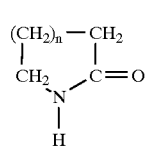

(wherein n is an integer of 1 to 3). Representative examples of the compound are 2-pyrrolidone, δ-valerolactam and ε-caprolactam. Of these, 2-pyrrolidone and ε-caprolactam are preferred.

The alkali metal alcoholate, which is the catalyst used in the present invention, is represented by the following general formula (II):

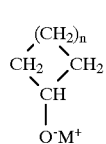

(wherein M is an alkali metal atom, and n is an integer of 2 to 5). Specific examples thereof are metal alcoholates derived from an alicyclic alcohol such as cyclopentanol, cyclohexanol, cycloheptanol or cyclooctanol and an alkali metal such as sodium, potassium or lithium. Potassium cyclohexyl alcoholate and sodium cyclohexyl alcoholate are preferred, and potassium cyclohexyl alcoholate is more preferred.

The alkali metal alcoholate can be produced by a known process, for example, by a reaction of an alcohol with an alkali metal hydroxide. In this reaction, since water is generated as a by-product, the alkali metal alcoholate is obtained ordinarily as a hydrous alcohol solution. In the present invention, the alkali metal alcoholate may be used as a solution obtained by removing water from the reaction mixture, or as a solid obtained by removing the alcohol from the solution.

The amount of the catalyst used in the reaction of a lactam with acetylene is 0.001 to 0.2, preferably 0.01 to 0.10 in terms of the molar ratio over the lactam. The concentration of the catalyst in the reaction system is 0.5 to 30% by weight, preferably 1 to 15% by weight.

The temperature of the reaction of a lactam with acetylene is not particularly restricted, but is ordinarily 80 to 200° C., preferably 120 to 180° C.

The time of the reaction differs depending upon various parameters such as reaction temperature, acetylene partial pressure and the like but, in the case of batchwise operation, is ordinarily 2 to 30 hours, preferably 5 to 15 hours.

In the present process, the acetylene partial pressure is ordinarily 0 to 10 kg/cm²·G, preferably 0 to 4 kg/cm²·G, more preferably 0 to 1.7 kg/cm²·G. Although a higher acetylene partial pressure gives a higher reaction rate, an as-low-as-possible acetylene partial pressure is preferred in order to prevent acetylene decomposition and explosion. In a reaction in which acetylene takes part, use of a low reaction pressure offers a big advantage from a safety standpoint.

A synthesis reaction using acetylene as a raw material is generally conducted by feeding, together with acetylene, an inert gas such as nitrogen, argon or propane to dilute acetylene and minimize the risk of the explosion. In the present process, dilution of acetylene with an inert gas is not necessary when the reaction is conducted at a low pressure.

In the present process, the reactor type can be any as long as the reactor used can give rise to a gas-liquid contact reaction. There can be mentioned, for example, a packed tower, a bubble column, an agitated vessel, a spray tower and a plate column. A combination thereof may be used. In order to allow the reaction to proceed favorably, a reactor capable of carrying out gas-liquid contact, namely gas-liquid counter current contact sufficiently, is preferred particularly.

The reaction of the present process may be conducted batchwise or continuously. In the case of continuous reaction, it is conducted according to, for example, a flow chart of FIG. 1. The steps of FIG. 1 comprises two steps, i.e. (1) a step for synthesis of N-vinyllactam (N-vinyllactam is hereinafter referred to simply as vinyllactam, in some cases) and (2) a step for distillation and separation of said product.

Specifically, into a reactor 5 are continuously fed raw material acetylene through an acetylene-feeding pipe 1 and a catalyst/a raw material lactam through a catalyst/lactam-feeding pipe 2; simultaneously therewith are continuously taken out the reaction mixture through a reaction mixture-taking out pipe 3 and a waste gas through a waste gas-taking out pipe 4; the reaction mixture taken out from the reactor 5 through the reaction mixture-taking out pipe 3 is fed into the intermediate section of a distillation tower 6; from the top of the distillation tower 6 is taken out a fraction composed mainly of a vinyllactam, through an N-vinyllactam-taking out pipe 8, and from the bottom of the distillation tower 6 is taken out an unreacted lactam and the catalyst dissolved in the lactam through a catalyst/unreacted lactam-taking out pipe 7; and the unreacted lactam and the catalyst taken out are returned into the catalyst/lactam-feeding pipe 2 or are fed directly into the reactor 5, for circulation.

The individual steps are described in more detail below.

First Step

This step is a step for reacting raw materials, namely a lactam and acetylene, using an alkali metal alcoholate as a catalyst. Acetylene and a catalyst/a lactam are fed into a reactor. Meanwhile, a reaction mixture, and a waste gas composed mainly of acetylene are taken out from the reactor. Feeding of acetylene into the reactor is conducted continuously so that the amount fed becomes equal to the total of the amount consumed in the reaction and the amount taken out in the waste gas and an intended reaction pressure is kept.

Feeding of the catalyst/the lactam into the reactor is made so that the catalyst concentration in the feed (the catalyst/the lactam) becomes equal to the catalyst concentration in the liquid phase of the reactor at the start of the reaction, whereby the reaction system can be kept in a constant and stable state. By feeding the lactam so that the liquid phase volumes of the reactor and the distillation tower become each constant, the catalyst concentration in the reaction mixture remains constant because the catalyst is nonvolatile and is not exhausted.

The reaction mixture is taken out continuously from the reactor so that there takes place no accumulation of the vinyllactam in the reactor. The concentration of the vinyllactam in the reaction mixture is kept preferably at 0.01 to 2.0 moles, more preferably at 0.05 to 1.5 moles per litter of the reaction mixture.

The waste gas is taken out from the reactor in order to remove low-boiling substances which are generated as by-products from the gas phase. Therefore, taking out of the low-boiling substances is not necessary when there is no accumulation of the low-boiling substances in the gas phase.

Second Step

In this step, the reaction mixture taken out from the reactor is subjected to distillation in a distillation tower, and a fraction composed mainly of a vinyllactam is taken out from the tower top, and the catalyst/the unreacted lactam are taken out from the tower bottom.

As the type of the distillation tower usable in the present process, there can be mentioned, for example, a flash distillation tower, a plate column and a packed tower. However, use of a rectifier is preferred in order to increase the vinyllactam concentration in the distillate taken out from the top and also in order to minimize the vinyllactam concentration in the catalyst/the unreacted lactam taken out from the bottom. The rectifier preferably has a certain number of theoretical plates, ordinarily 2 to 20 plates, preferably 5 to 20 plates. The number of theoretical plates used differs depending upon the reflux ratio used and cannot be specified at a fixed level. Thus, the overall conversion and selectivity of raw material lactam in the first step and the second step can be increased.

The distillation temperature is desired to be as close as possible to the reaction temperature in view of the thermal efficiency of distillation and is preferred to be 80 to 200° C. The distillation pressure is generally preferred to be lower than the reaction pressure and is controlled so that a vinyllactam distillation rate equal to the vinyllactam formation rate in the reactor is achieved within the distillation temperature employed. A lower distillation pressure enables use of a lower distillation temperature and consequently can suppress side reactions, vinyllactam polymerization, etc.

The catalyst/the unreacted lactam taken out from the distillation tower bottom is circulated to the reactor or the catalyst/lactam-feeing pipe, as it is or after adding a fresh lactam as necessary for concentration control.

DESCRIPTION OF PREFERRED EMBODIMENTS

The present invention is described specifically below by way of Examples. However, these Examples are presented as illustrative only and the present invention is in no way restricted by the Examples. In the following Examples and Comparative Examples, % is by weight.

Reference Example 1 (Production of Catalyst)

Into a dried reactor (a stainless steel autoclave having an internal volume of 1 litter) were fed 248.3 g (2.48 moles) of cyclohexanol and 25.1 g (0.45 mole) of flake-like potassium hydroxide. The gas inside the reactor was replaced by nitrogen. Then, the reactor contents were heated to 140° C. with stirring to give rise to a reaction, and an excess of cyclohexanol and the water generated by the reaction were removed by distillation. That is, 93.6 g (0.94 mole) of cyclohexanol and 8.1 g (0.45 mole) of water were removed by distillation to obtain a solution of potassium cyclohexyl alcoholate dissolved in cyclohexanol (the solution is called catalyst A).

Reference Example 2 (Production of Catalyst)

A solution of potassium cyclohexyl alcoholate dissolved in cyclohexanol, produced in the same manner as in Reference Example 1, was subjected to distillation at 108° C. under a vacuum of 10 mmHg to remove the cyclohexanol contained in the solution, whereby a solid potassium cyclohexyl alcoholate (catalyst B) was obtained.

EXAMPLE 1

In a dried reactor (a stainless steel autoclave having an internal volume of 1 litter) were fed 455.0 g (5.29 moles) of 2-pyrrolidone and 62.2 g (0.45 mole) of catalyst B (potassium cyclohexyl alcoholate) obtained in Reference Example 2. The gas inside the reactor was thoroughly replaced by nitrogen and further by acetylene to introduce, into the reactor, 0.30 kg/cm$^2$·G of acetylene. The reactor contents were heated at that pressure with stirring at 900 rpm, and a reaction was allowed to take place at 140° C. for 4 hours. Part of the reaction mixture was collected for analysis by gas chromatography, which indicated that the conversion of 2-pyrrolidone was 55.3%. The reaction was continued for a further 5 hours and the reaction mixture was analyzed, which indicated that the conversion of 2-pyrrolidone was 80.9% and the selectivity into N-vinylpyrrolidone was 92.0%.

Comparative Example 1

A reaction of 2-pyrrolidone with acetylene was conducted under the same conditions as in Example 1 except that catalyst B was replaced by 50.0 g (0.45 mole) of potassium t-butoxide which is an alcoholate of a tertiary alcohol. After 4 hours from the start of the reaction, part of the reaction mixture was collected and analyzed by gas chromatography, which indicated that the conversion of 2-pyrrolidone was 26.7%. The reaction was continued for a further 5 hours and the reaction mixture was analyzed, which indicated that the conversion of 2-pyrrolidone was 35.5% and the selectivity into N-vinylpyrrolidone was 89.2%.

EXAMPLE 2

In a reactor were fed 171.7 g (0.45 mole as potassium cyclohexyl alcoholate) of catalyst A produced in Reference Example 1 and 345.3 g (4.06 moles) of 2-pyrrolidone. Then, acetylene was introduced into the reactor, and a reaction was conducted for 9 hours in the same manner as in Example 1. The resulting product was analyzed, which indicated that the conversion of 2-pyrrolidone was 56.9% and the selectivity into N-vinylpyrrolidone was 92.0%.

EXAMPLE 3

Into a reactor (a 10 litter stainless steel autoclave) provided with a stirrer were fed 173 g (1.25 moles) of catalyst B produced in the same manner as in Reference Example 2 and 4,870 g (57.2 moles) of 2-pyrrolidone. A reaction was allowed to take place for 1 hour under the same temperature and pressure conditions as in Example 1. Then, the reaction mixture was taken out continuously from the reactor at a rate of 41.5 ml/min, and fresh 2-pyrrolidone was fed continuously into the reactor at a rate of 8.5 ml/min. The taken-out reaction mixture was fed continuously into an Oldershaw column having 5 theoretical plates and was subjected to distillation under the conditions of column inside pressure= 11 mmHg, column top temperature=116° C., column bottom temperature=125° C. and reflux ratio=4. From the column top was discharged an N-vinylpyrrolidone/2-pyrrolidone mixture composing mainly of N-vinylpyrrolidone at a rate of 8.5 ml/min; meanwhile, from the column bottom was taken out a solution comprising the catalyst and unreacted 2-pyrrolidone, at a rate of 33.0 ml/min, and the taken-out solution was circulated into the reactor. The above reaction and distillation was continued for 25 hours and the reaction mixture was analyzed, which indicated that the conversion of 2-pyrrolidone was 14.0% and the selectivity into N-vinylpyrrolidone was 98.0%.

In the process of the present invention, by using an alkali metal alcoholate of a particular alicyclic alcohol as the catalyst, an N-vinyllactam can be produced in a simple vinylation step alone at a relatively low acetylene partial pressure, at a high conversion and a high selectivity.

Further in the present process, by combining a vinylation step and a distillation step and circulating the used catalyst and unreacted lactam, an N-vinyllactam can be produced continuously and efficiently.

What is claimed is:

1. A process for producing an N-vinyllactam by reacting a lactam with acetylene, which comprises reacting a lactam represented by the following general formula (I):

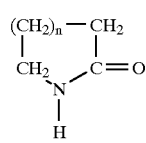
(I)

(wherein n is an integer of 1 to 3) with acetylene, in the presence of an alkali metal alcoholate catalyst represented by the following general formula (II):

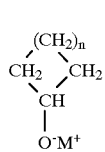
(II)

(wherein M is an alkali metal atom, and n is an integer of 2 to 5) at an acetylene partial pressure of 0 to 10 kg/cm²·G.

2. A process according to claim 1, wherein the lactam of the general formula (I) is 2-pyrrolidone, δ-valerolactam or ε-caprolactam.

3. A process according to claim 1, wherein the alkali metal alcoholate of the general formula (II) is a compound of the general formula (II) wherein M is potassium or sodium and n is 3.

4. A process according to claim 3, wherein M is potassium.

5. A process according to claim 1, wherein the acetylene partial pressure is 0 to 1.7 kg/cm²·G.

6. A process according to claim 1, wherein the reaction of a lactam of the general formula with acetylene is conducted at a temperature of 80 to 200° C.

7. A process for producing an N-vinyllactam by reacting a lactam with acetylene, which comprises reacting, in a reactor, a lactam represented by the following general formula (I):

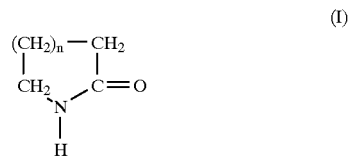
(I)

(wherein n is an integer of 1 to 3) with acetylene, in the presence of an alkali metal alcoholate catalyst represented by the following general formula (II):

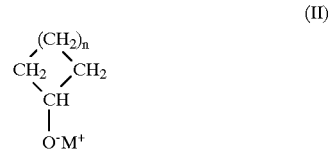
(II)

(wherein M is an alkali metal atom, and n is an integer of 2 to 5) at an acetylene partial pressure of 0 to 10 kg/cm²·G. then continuously taking out the reaction mixture containing the catalyst from the reactor, feeding it into a distillation tower, recovering a fraction composed mainly of an N-vinyllactam from the tower top, taking out a liquid composed mainly of the lactam and the catalyst from the tower bottom, and circulating the liquid into the reactor.

* * * * *